United States Patent
Sabbagh

[11] Patent Number: 5,944,518
[45] Date of Patent: Aug. 31, 1999

[54] DEVICE FOR CORRECTING JAW AND TOOTH MALPOSITIONING

[76] Inventor: Aladin Sabbagh, Stettiner Str. 19, 90425 Nurnburg, Germany

[21] Appl. No.: 09/044,572

[22] Filed: Mar. 19, 1998

[30] Foreign Application Priority Data

Mar. 19, 1997 [DE] Germany .......................... 297 04 990

[51] Int. Cl.⁶ ...................................................... A61C 7/36
[52] U.S. Cl. ................................................................ 433/19
[58] Field of Search ................................... 433/18, 19, 21

[56] References Cited

U.S. PATENT DOCUMENTS

| | | | |
|---|---|---|---|
| 3,618,214 | 11/1971 | Armstrong | 433/19 |
| 3,798,773 | 3/1974 | Northcutt | 433/19 |
| 4,795,342 | 1/1989 | Jones | 433/19 |
| 5,074,784 | 12/1991 | Sterrett et al. | 433/19 |
| 5,352,116 | 10/1994 | West | 433/19 |
| 5,562,445 | 10/1996 | De Vincenzo et al. | 433/19 |
| 5,678,990 | 10/1997 | Rosenberg | 433/19 |
| 5,711,667 | 1/1998 | Vogt | 433/19 |
| 5,738,514 | 4/1998 | De Vincenzo et al. | 433/19 |
| 5,829,975 | 11/1998 | Gold | 433/19 |

FOREIGN PATENT DOCUMENTS 915317  11/1946  France ..................... 433/21

*Primary Examiner*—Ralph A. Lewis
*Attorney, Agent, or Firm*—Pearne, Gordon, McCoy & Granger LLP

[57] ABSTRACT

The invention relates to a device for correcting jaw and tooth malpositioning, with a jacket tube 1 at whose jacket tube end E1 a first securing element 2 is provided, a tube 4 which is telescopically displaceable inside the jacket tube 1 and in which a rod 6 is guided in a telescopically displaceable manner, said rod 6 having a second securing element 7 provided at the first rod end E4. To increase the application possibilities of such a device, the invention provides that a spring 5 received in the jacket tube 1 be supported with its first spring end F1 in proximity to the jacket tube end E1 and with its second spring end F2 at the opposite first tube end E2.

11 Claims, 4 Drawing Sheets

DEVICE FOR CORRECTING JAW AND TOOTH MALPOSITIONING

BACKGROUND OF THE INVENTION

The invention relates to a device for correcting jaw and tooth malpositioning in accordance with the preamble of claim 1.

Such a device is known from the brochure "EUREKA Spring!" published in 1995 by the company EUREKA Spring, San Luis Obispo, USA, and from DE 196 24 654 A1. In said device, a rod is received in a telescopically displaceable manner in a tube which is closed at one end. A spring is provided between the closed tube end and the opposite rod end. The rod has a defined length; it is connected nonreleasably to the tube. The elastic shear force acting on the rod is predetermined by the spring being used in each case.

Since neither the spring nor the tube can be readily altered, the known device cannot be universally employed. It is suited exclusively as an orthodontic appliance, i.e. for correction of malpositioning of the teeth. A further disadvantage of this device lies in the fact that malodorous deposits accumulate in the inside of the device and are detrimental to oral hygiene. Finally, the device cannot be activated, i.e. readjustment of the device by changing the spring force after partial correction is not possible.

In order to correct jaw malpositioning, i.e. orthopedic correction of an overbite or underbite, DE 37 98 773 and DE 45 55 095 also disclose the so-called Herbst hinge. This is a telescoping device which is secured on the outside of the tooth in the upper jaw and lower jaw in each case. The Herbst hinge only permits those jaw movements which counter the malpositioning of the jaw. When biting, the Herbst hinge causes abrupt blocking. This is experienced as an unpleasant sensation by the patient and occasionally leads to damage. The Herbst hinge is not suited for correction of malpositioning of the teeth. A further disadvantage of the Herbst hinge lies in the fact that it can loosen if the mouth is opened too wide.

The object of the present invention is to remedy the disadvantages of the prior art. The aim in particular is to make available a universally applicable device which is suited both for correction of malpositioning of the jaw and also malpositioning of the teeth. The device is also intended to be simple to activate and easily repairable.

This object is achieved by the features described herein. Advantageous embodiments of the invention emerge from additional features described wherein.

SUMMARY OF THE INVENTION

The arrangement according to the invention permits the separate exchange of tube, spring and rod. In this way, the device can be activated in a simple manner; the pressure force and the length of the device can be adapted to the particular correction to be performed.

According to one embodiment feature, the spring is secured releasably to the jacket tube in proximity to the jacket tube end, in which case a thread suitable for engagement of the spring is advantageously provided on the inner wall of the jacket tube in proximity to the jacket tube end. The second spring end is expediently connected nonreleasably to the first tube end. This permits particularly simple assembly and dismantling of the tube carrying the spring. Loosening when the mouth is opened wide is also prevented.

In order to prevent the accumulation of deposits in the inside of the device, the first tube end can be open. Furthermore, it is considered advantageous for the rod to be designed longer than the tube, so that the second rod end engages through the tube end in the telescoped state. The jacket tube end is also advantageously open.

The rod can be designed with such a length that it also engages through the jacket tube end in the telescoped state. In this way, debris which gets into the inside of the device can, if appropriate assisted by displacement movements of the rod, be removed again via the jacket tube end.

BRIEF DESCRIPTION OF THE SEVERAL VIEWS OF THE DRAWINGS

Illustrative embodiments of the invention are explained in greater detail below with reference to the drawing, in which.

DETAILED DESCRIPTION OF THE INVENTION

Figure 1:
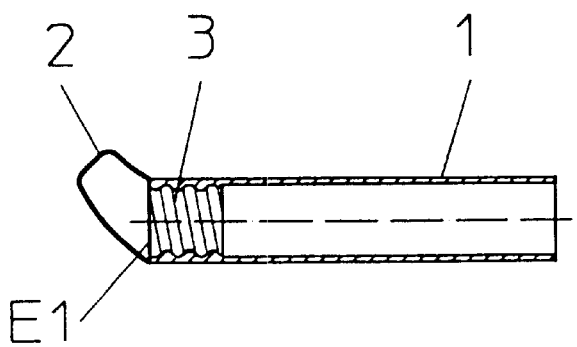
FIG. 1 shows a diagrammatic cross section through a jacket tube.

FIG. 1 shows a jacket tube 1. A first securing element is provided at the jacket tube end E1. A thread 3 is located on the inner wall of the jacket tube 1, in proximity to the jacket tube end E1.

Figure 2:
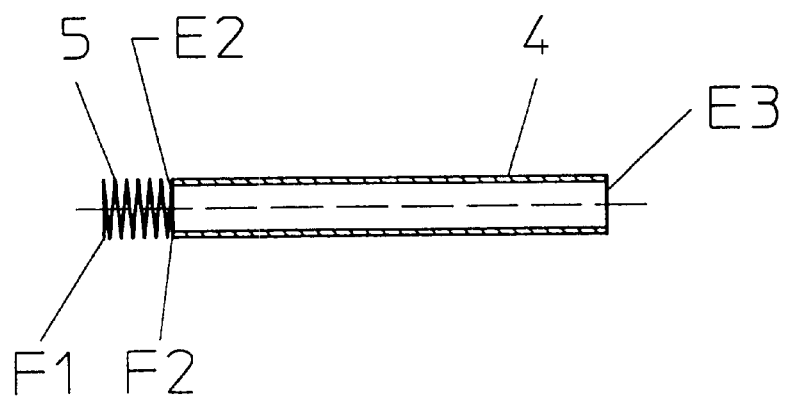
FIG. 2 shows a diagrammatic cross section through a first tube.
Figure 3:
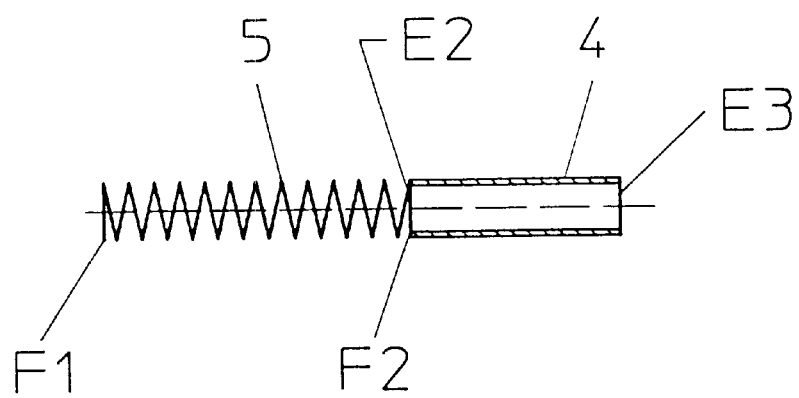
FIG. 3 shows a diagrammatic cross section through a second tube.

FIGS. 2 and 3 show a first and a second tube 4. A spring with a first spring end F1 is arranged with a second spring end F2 on a first tube end E2, e.g. by welding, soldering or adhesive bonding. A second tube end is designated by E3.

Figure 4:
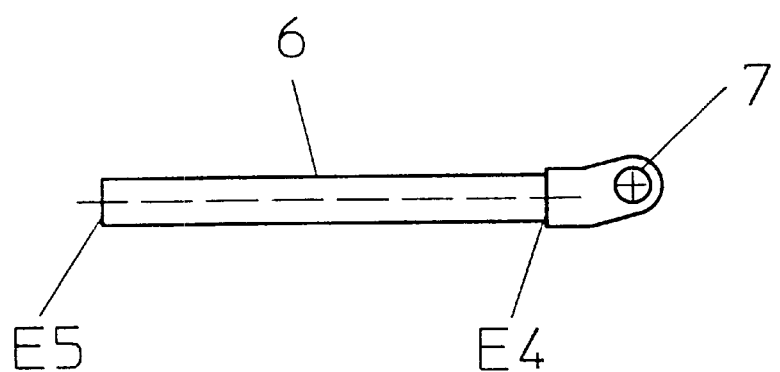
FIG. 4 shows a diagrammatic cross section through a rod.

FIG. 4 shows a rod 6 at whose first rod end E4 a second securing element 7 is located. A second rod end is designated by E5.

Figure 5:
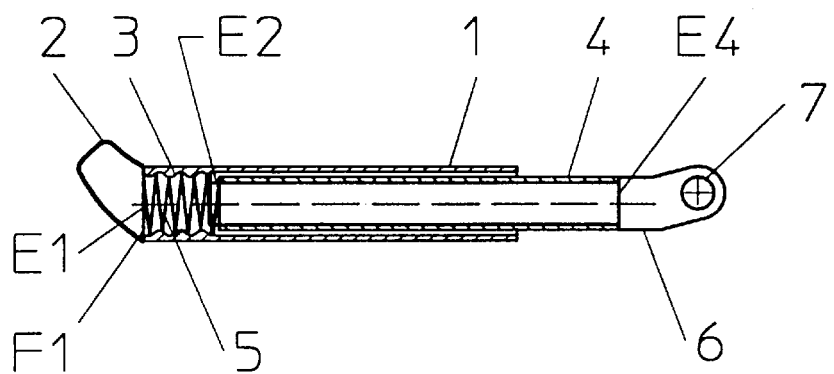
FIG. 5 shows a diagrammatic cross section through a first device.

FIG. 5 shows a diagrammatic cross section through a first device. The tube 4 is pushed into the jacket tube 1 as far as a limit stop formed at the first rod end E4. The spring 5 engages with its first spring end F1 in the thread 3. The rod 6 is received in a telescopic manner in the tube 4. The tube 4 is here designed several times longer than the spring 5.

Figure 6:
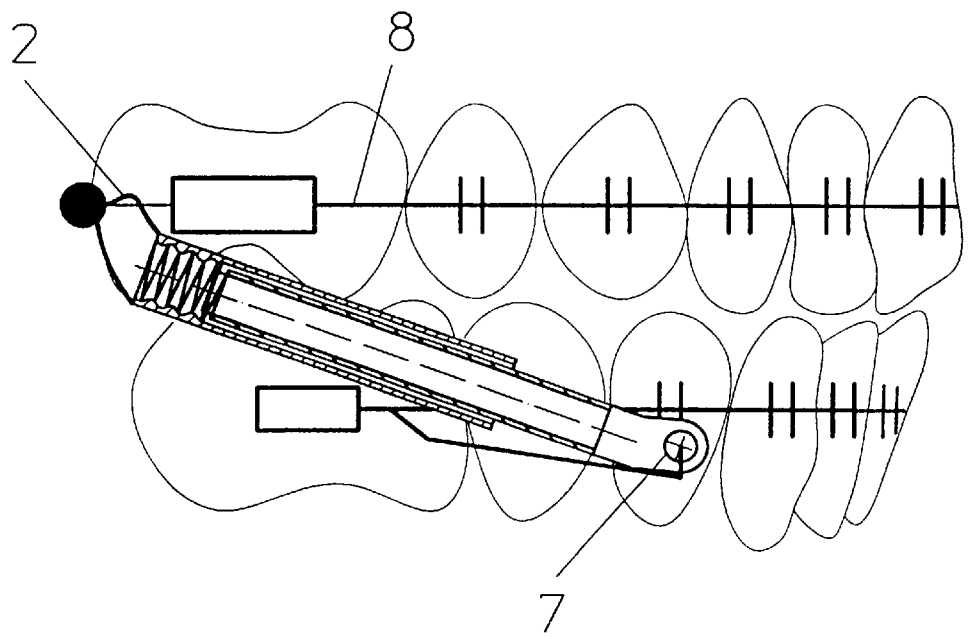
FIG. 6 shows the arrangement of the first device for correction of an overbite.

FIG. 6 shows diagrammatically the arrangement of the device according to FIG. 5 for correction of an overbite. The device is secured with the first securing element 2 on a jaw-regulating appliance 8 in the area of an upper buccal tooth. The second securing element 7 is arranged in proximity to one of the lower front teeth.

Figure 7:
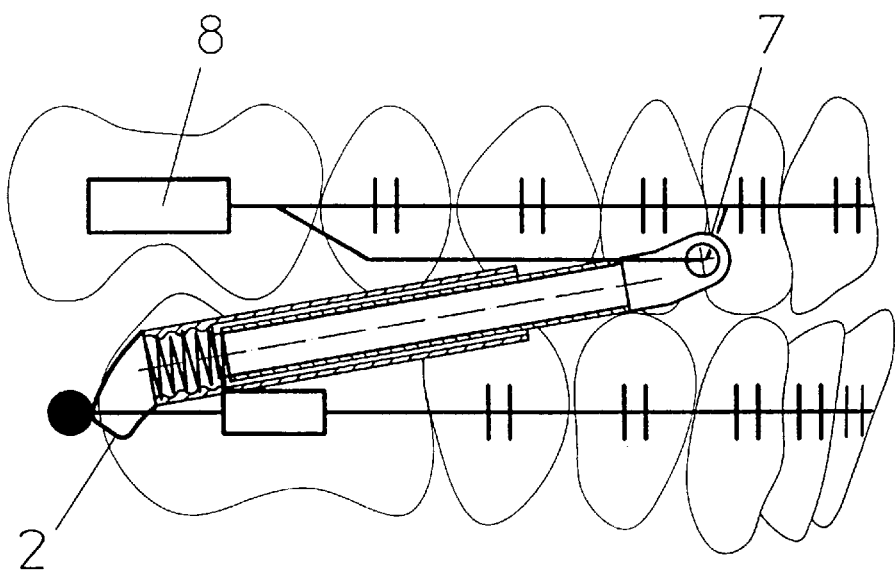
FIG. 7 shows the arrangement of the first device for correction of an underbite.

FIG. 7 shows diagrammatically the arrangement of the device according to FIG. 5 for correction of an underbite.

Here, the second securing element 7 is arranged in the area of the upper front teeth and the first securing element 2 is arranged in proximity to the lower back teeth.

Figure 8:
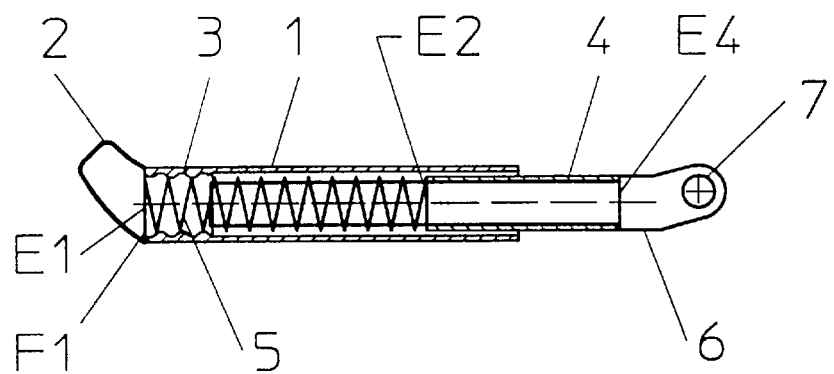
FIG. 8 shows a diagrammatic cross section through a second device.

FIG. 8 shows a second device. Here, the spring 5 is designed almost twice as long as the tube 4.

Figure 9:
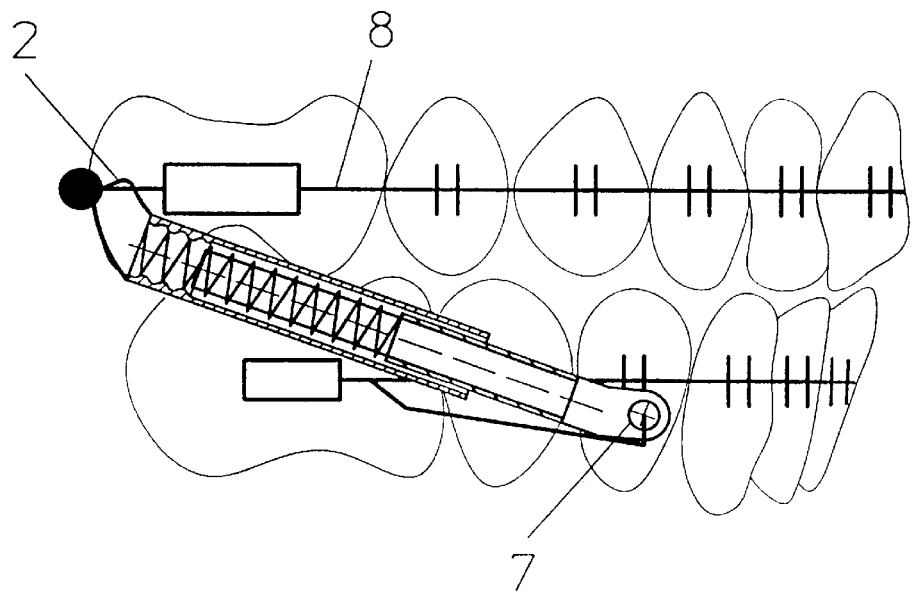
FIG. 9 shows the arrangement of the second device for correction of an overbite as a result of malpositioning of the teeth.
Figure 10:
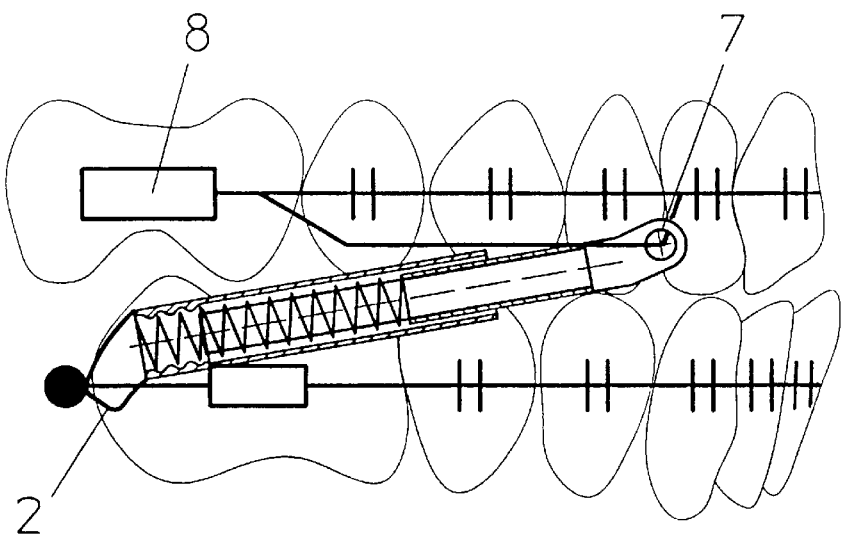
FIG. 10 shows the arrangement of the second device for correction of an underbite as a result of malpositioning of the teeth.

FIGS. 9 and 10 show, analogously to FIGS. 6 and 7, the arrangement of the second device for correction of an overbite and underbite.

The function of the first device is as follows:

As the jaw is closed, the rod 6 moves telescopically into the tube 4. The rod 6 first strikes against the second tube end E3 via a limit stop provided at the first rod end E4. The onward closure movement of the jaw is slowed down by the action of the spring 5 and is stopped upon complete compression of the spring 5. An abrupt blocking, which is an unpleasant sensation for the patient, and damage to the device are avoided in this way. The length of the tube 4 and/or the rod 6 provides the desired extent of jaw correction in such a way that the mandible is forced forward during biting.

The function of the second device is as follows:

Here, the length of the rod 6 is chosen such that when the jaw is closed the spring 5 is not completely compressed. With the jaw closed, the force of the spring 5 acts via the rod 6 on the rows of teeth of the lower jaw and upper jaw. Thus, an overbite or underbite caused by malpositioning of the teeth can be corrected.

The device can be employed universally. By simply exchanging the tube 4 with the spring 5 for a tube having another length and a spring having another length and/or spring constant, the device can be adapted to the particular correction required.

As a result of the open design of the jacket tube end E1 and of the first tube end E2, it is not possible for malodorous deposits to accumulate in the device.

| References |
| --- |
| 1 Jacket tube |
| 2 First securing element |
| 3 Thread |
| 4 Tube |
| 5 Spring |
| 6 Rod |
| 7 Second securing element |
| 8 Jaw-regulating appliance |
| E1 Jacket tube end |
| E2 First tube end |
| E3 Second tube end |
| E4 First rod end |
| E5 Second rod end |
| F1 First spring end |
| F2 Second spring end |

I claim:

1. Device for correcting jaw and tooth malpositioning, with a jacket tube (1) having a jacket tube end (E1) provided with a first securing element (2), a tube (4) which is telescopically displaceable inside the jacket tube (1) and a rod (6) disposed in the tube and guided in the jacket tube in a telescopically displaceable manner, said rod (6) having a second securing element (7) provided at a first rod end (E4), characterized in that a spring (5) received in the jacket tube (1) is supported with a first spring end (F1) on the jacket tube (1) and adjacent the jacket tube end (E1) and with a second spring end (F2) at an opposite first tube end (E2).

2. Device according to claim 1, in which the spring (5) is secured releasably on the jacket tube (1).

3. Device according to claim 2, in which a thread (3) suitable for the engagement of the spring (5) is provided on the inner wall of the jacket tube (1) adjacent the jacket tube end (E1).

4. Device according to one of the preceding claims, in which the second spring end (F2) is connected nonreleasably to the first tube end (E2).

5. Device according to claim 4, in which the first securing element (2) and the second securing element (7) can be coupled to an orthodontic appliance (8) connected to the teeth.

6. Device according to claim 5, in which the first tube end (E2) is open.

7. Device according to claim 6, in which the rod (6) is designed longer than the tube (4), so that the second rod end (E5) engages through the first tube end (E2) in the telescoped state.

8. Device according to claim 7, in which the jacket tube end (E1) is open.

9. Device for correcting jaw and tooth malpositioning, with a jacket tube (1) having a jacket tube end (E1) provided with a first securing element (2), a tube (4) which is telescopically displaceable inside the jacket tube (1) and a rod (6) disposed in the tube and guided in the jacket tube in a telescopically displaceable manner, said rod (6) having a second securing element (7) provided at a first rod end (E4), characterized in that a spring (5) received in the jacket tube (1) is supported with a first spring end (F1) on the jacket tube (1) and adjacent the jacket tube end (E1) and with a second spring end (F2) at an opposite first tube end (E2), wherein the jacket tube end (E1) is open.

10. Device according to claim 9, in which the first tube end (E2) is open.

11. Device according to claim 10, in which the rod (6) is designed longer than the tube (4), so that the second rod end (E5) engages through the first end tube (E2) in the telescoped state.

* * * * *

UNITED STATES PATENT AND TRADEMARK OFFICE
CERTIFICATE OF CORRECTION

PATENT NO. : 5,944,518
DATED : August 31, 1999
INVENTOR(S) : Sabbagh

It is certified that error appears in the above-indentified patent and that said Letters Patent is hereby corrected as shown below:

Column 1, Line 48, delete "wherein" and insert --herein--.

Column 2, Line 46, after "spring", insert --5--.

Signed and Sealed this

Second Day of May, 2000

Q. TODD DICKINSON

*Attest:*

*Attesting Officer*   *Director of Patents and Trademarks*